(12) United States Patent
Suddaby

(10) Patent No.: US 6,332,895 B1
(45) Date of Patent: Dec. 25, 2001

(54) EXPANDABLE INTERVERTEBRAL FUSION IMPLANT HAVING IMPROVED STABILITY

(76) Inventor: Loubert Suddaby, 76 Tanglewood Dr., Orchard Park, NY (US) 14127

(*) Notice: Subject to any disclaimer, the term of this patent is extended or adjusted under 35 U.S.C. 154(b) by 0 days.

(21) Appl. No.: 09/521,383

(22) Filed: Mar. 8, 2000

(51) Int. Cl.[7] .................................................. A61F 2/44
(52) U.S. Cl. ................................................. 623/17.11
(58) Field of Search ........................ 623/17.15, 17.11, 623/17.16

(56) References Cited

U.S. PATENT DOCUMENTS

| | | |
|---|---|---|
| 5,505,732 | 4/1996 | Michelson . |
| 5,653,762 | 8/1997 | Pisharodi . |
| 5,665,122 | 9/1997 | Kambin . |
| 5,683,463 | 11/1997 | Godefroy et al. . |
| 5,865,848 | * 2/1999 | Baker ............................ 623/17 |
| 5,980,522 | * 11/1999 | Koros et al. ..................... 606/61 |
| 6,174,344 | * 1/2001 | Suddaby ...................... 623/17.11 |

* cited by examiner

Primary Examiner—Corrine McDermott
Assistant Examiner—Thomas Barrett
(74) Attorney, Agent, or Firm—Shoemaker and Mattare

(57) ABSTRACT

An expandable intervertebral implant includes two separate shells having corrugated mating surfaces which resist compression and shifting when the parts are distracted by a special installation tool. The shells include two planar wings which provide a large bearing area against adjacent vertebral endplates to prevent the implant from sinking into cancellous bone.

5 Claims, 4 Drawing Sheets

EXPANDABLE INTERVERTEBRAL FUSION IMPLANT HAVING IMPROVED STABILITY

BACKGROUND OF THE INVENTION

This invention relates to an expandable fusion implant suitable for anterior approaches to the spinal column. The class of implements to which this invention pertains serve to stabilize adjacent vertebral elements, thereby facilitating the development of a bony union between them and thus long term spinal stability.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvic or sacral region which are normally fused together and form the back part of the pelvis. This column of bones is critical for protecting the delicate spinal cord and nerves, and for providing structural support for the entire body.

Between the vertebral bones themselves exist soft tissue structures—discs—composed of fibrous tissue and cartilage which are compressible and act as shock absorbers for sudden downward forces on the upright column. The discs allow the bones to move independently of each other, as well. The repetitive forces which act on these intervertebral discs during repetitive day-to-day activities of bending, lifting and twisting cause them to break down or degenerate over time.

Presumably because of humans' upright posture, their intervertebral discs have a high propensity to degenerate. Overt trauma, or covert trauma occurring in the course of repetitive activities disproportionately affect the more highly mobile areas of the spine. Disruption of a disc's internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability such as spinal curvature.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prostheses in various forms have therefore been used to provide immediate stability and to protect and preserve an environment that fosters growth of grafted bone such that a structurally significant bony fusion can occur.

U.S. Pat. Nos. 5,505,732, 5,653,762, 5,665,122,and 5,683,463 describe different prior spinal implants. The implant shown in U.S. Pat. No. 5,483,463 is hollow and tubular, with communicating windows in the top and bottom surfaces. External ribs, which may be serrated, stabilize the implant once it is inserted between the vertebrae. In U.S. Pat. No. 5,665,122, an intervertebral cage is rendered expandable by a wedging mechanism. The degree of expansion is rather limited, however. U.S. Pat. Nos. 5,653,762 and 5,505,732 show shaft-type tools used for installing implants. The prior devices do not enable one to achieve great ranges of implant height.

Limitations of most present-day intervertebral implants are significant and revolve largely around the marked variation in disc space shape and height that results from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2–3 mm must be added on either end, resulting in a final implant size of 24–26 mm. During implantation from an anterior approach (from the front of the body), excessive retraction (pulling) is often required on the great blood vessels which greatly enhances the risk of devastating complications such as vascular tears or thrombosis. Compromising on implant size risks sub-optimal stability or a loose implant, which has a greater chance for migration within or expulsion from the disc space.

Because of difficulty with retraction of vascular elements and inadequate anterior exposure, single cylindrical devices are often implanted to compensate for the inadequate exposure required to implant paired devices. A single cylindrical implant has the disadvantage of allowing rotation of vertebral elements around the cylindrical axis of the implant. This in turn results in a degree of lateral instability ("barrel roll") which may result in non-union at the fusion site.

To counteract this problem, surgeons have attempted to place a single cylindrical fusion device at an oblique angle across the disc space. While this eliminates some of the barrel roll effect laterally, movement is still possible and can result in non-union. Other surgeons have recommended an oblique angled implement backup up with posterior pedicle screws, but this approach has the distinct disadvantage of requiring a major secondary surgical procedure from the posterior approach to achieve this. In addition, a single intervertebral implant placed centrally contacts the weakest part of the vertebral endplate which means little endplate support is present to retain the implant in position. Frequently, these lone implants will sink or subside into the soft cancellous portion of the vertebral body above or below. This subsidence means that the annular tension provided by the implant is lost and instability at the segment with concomitant progression to non-union at the fusion site occurs. Non-union is a disappointing consequence of this occurrence, and frequently results in the need for further surgical procedures.

Obviously, it would be of value to have a single stand-alone implant that could be introduced anteriorly without the drawbacks of rotational instability about the cylindrical or longitudinal axis of the implant. It would also be desirable to have greater endplate support provided by the implant to prevent subsidence into the adjacent vertebral cancellous bone, and the resultant loss of stability consequent with this. Having an expandable implant which can adjust to variabilities in disc space height would be an added benefit.

SUMMARY OF THE INVENTION

It is the object of this invention to provide an expandable intervertebral fusion implant that is both simple to manufacture and simple to use as a single stand-alone entity in daily clinical surgical practice while remaining versatile enough to address the complex biologic and pathologic variability of the human spine.

It is also intended that this device address the present problems inherent to single fusion implants: rotational instability and subsidence into adjacent vertebral elements.

To achieve these objectives, a pair of semicylindrical shells are distracted inside an intervertebral space that has been appropriately prepared for fusion from an anterior approach. These semi-cylindrical shells have lateral wings which sit juxtaposed to the end plates of the vertebral body to provide a large surface area for adjacent end plate support. Each wing makes up at least 20% of the width of the implant, preferably at least 25%. The shells are distracted with an expandable installation tool and the shells are held apart by ratchets or corrugations in their side walls to permit optimal tensioning of the annular support ligaments, and hence immediate stability. The installation tool is then unscrewed and disengaged, leaving the component parts as a stable assembly that can be packed with bone to promote osseous union.

This invention provides a superior stand-alone expandable intervertebral fusion implant ideally suited to anterior approaches to the spinal column (cervical, thoracic, lumbar). In addition, it allows variable expansion to optimally tauten annular ligamentous structures providing immediate stability without the need for secondary posterior surgical procedures. It also provides sufficient end plate support by means of lateral wings which prevent not only rotational instability inherent to other single cylindrical devices, but also prevents "subsidence instability" by distributing compressive and distractive forces over a larger surface area of end plate, thereby avoiding the sinking or subsidence of the implant into the adjacent soft cancellous bone.

The cylindrical implant is split horizontally so that the cranial (upper) and caudal (lower) shells that contact the vertebral bones above and below can be distracted, or spread apart, by a screw-type installation tool until optimal distraction of the vertebral elements and appropriate tension on the ligamentous structures is achieved. The installation tool is then retracted, allowing the two components to seat against one another and lock together, and the tool is then removed. The implant assembly is now packed with allograft or auto graft bone to allow long term bony union to develop between the vertebral elements.

The advantages provided by this invention also include (1) the fact that both the tool and the implant components are of simple manufacture, and (2), because of its expandable nature, this implant has the advantage of use in anterior approaches where space in minimal and the ability to retract vascular structures is compromised.

BRIEF DESCRIPTION OF THE DRAWINGS

In the accompanying drawings.

DESCRIPTION OF THE PREFERRED EMBODIMENT

Figure 1:
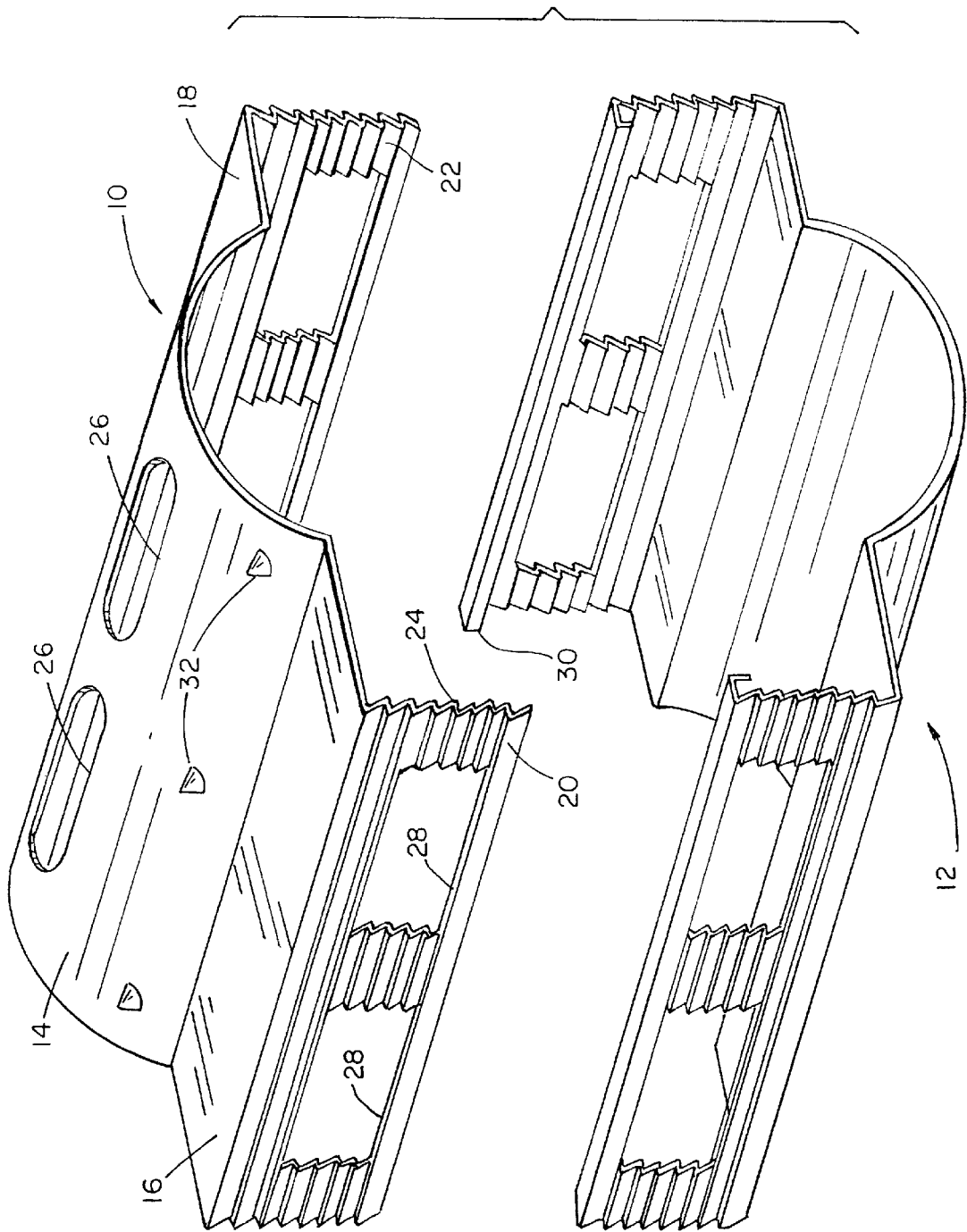
FIG. 1 is an exploded front elevation of an intervertebral fusion implant embodying the invention.

An expandable intervertebral fusion implant embodying the invention appears in FIGS. 1–5. The implant in every case comprises a pair of shells 10, 12 which when assembled (FIG. 2) form an implant assembly. Each shell comprises a central section 14, which is an arc of a cylinder, and a pair of wings 16, 18 extending in the same plane from opposite ends of the arc. Corrugated side walls 20, 22 extend parallel to one another from the outer edges of the wings. The corrugations 24, when viewed from the end, are seen to have to form of teeth which are raked in one direction so that they provide a ratcheting action when the shells are assembled. These walls also prevent the parts from shifting laterally.

One can see that, for each tooth, there is a ramping surface "R", which is oblique to the line of relative movement "L" (FIG. 3) of the shells, meeting an abutment surface "A" which is substantially perpendicular to the line of relative movement.

As shown in the exploded view of FIG. 1, each shell preferably has several windows to encourage interlocking bone growth. The preferred arrangement is a pair of oval central windows 26 in the curved central portion of each shell, and a pair of rectangular windows 28 in each side wall 20 or 22.

The skirts on the lower shell lie between those of the upper shell, when the device is oriented as in the drawings, so the inner skirts are those on the lower shell. Each of these inner skirts is provided with a protruding element, specifically a hooked flange 30, so that, if it becomes desired to removed the implant, the surgeon can grasp the flanges and draw them together to release the teeth from engagement and allow the implant to retract.

The spurs 32 adjacent the windows dig into the surfaces of the bones between which the implant is installed, and, together with compression forces from the spinal ligaments, prevent the shells from shifting lengthwise with respect to one another.

Figure 2:
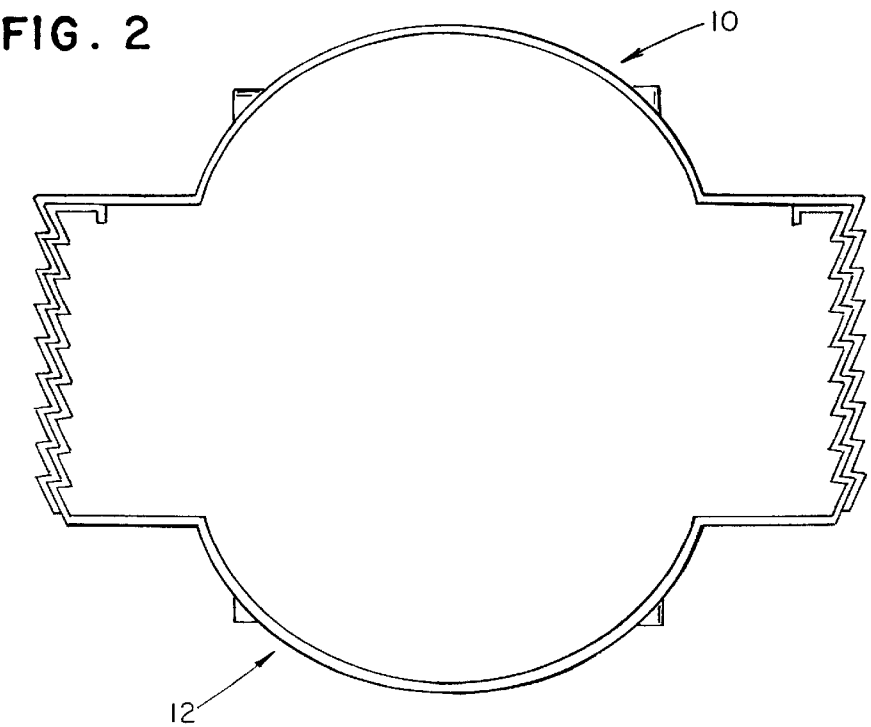
FIGS. 2 and 3 are front elevations of the implant, shown in retracted and expanded configurations, respectively.
Figure 3:
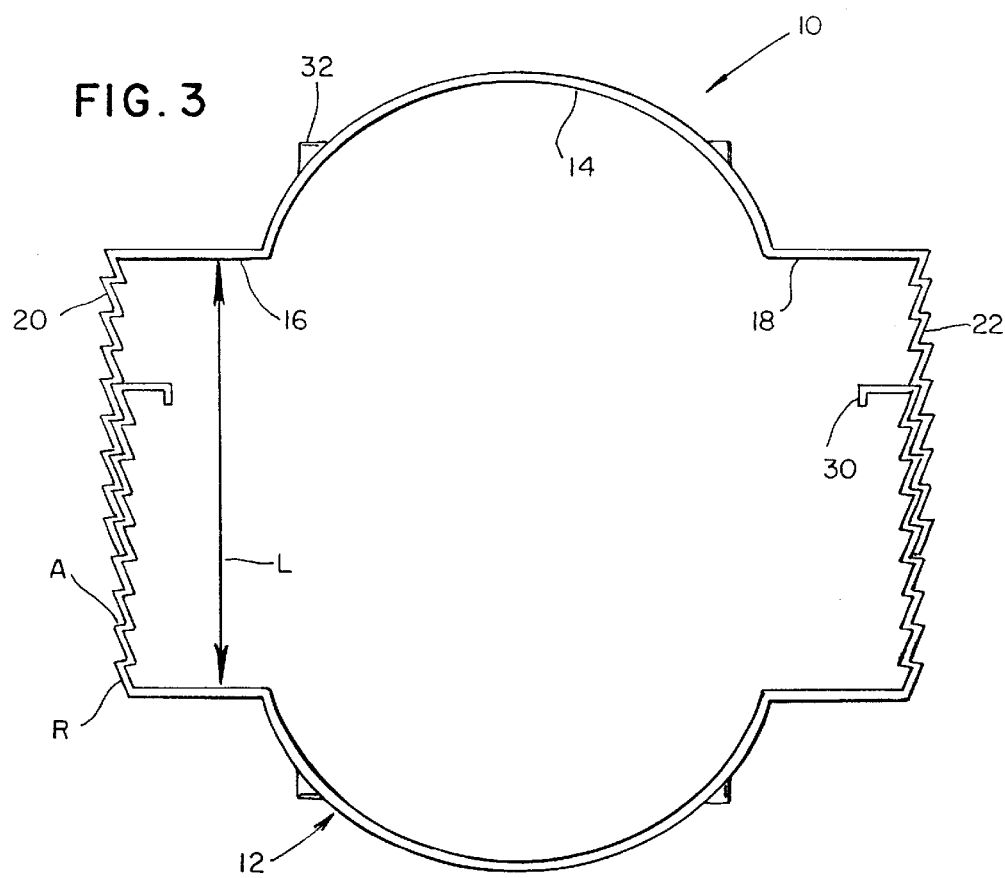

FIG. 2 shows the shells assembled, as close together as possible, as is done prior to installation by the surgeon. FIG. 3 shows the shell in an exemplary expanded configuration, as they would be following the installation described below.

The shells may be made of the same material, or different materials. Suitable materials include stainless steel, titanium, ceramic, graphite, carbon fiber material, and various plastics and composites of the foregoing. The selection of material may affect the dimensions or proportions of the parts somewhat, but is generally a matter of design choice.

Figure 4:
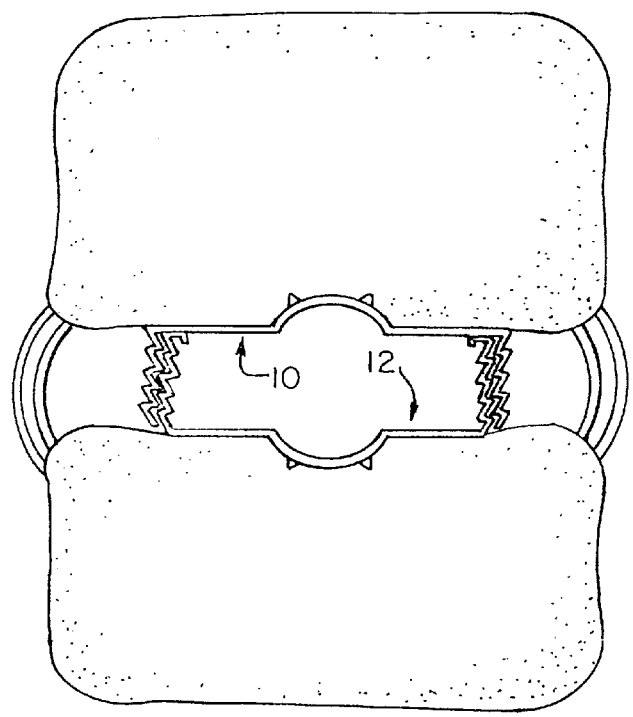
FIG. 4 is an anterior view of a pair of implants installed between two vertebrae, without expansion.
Figure 5:
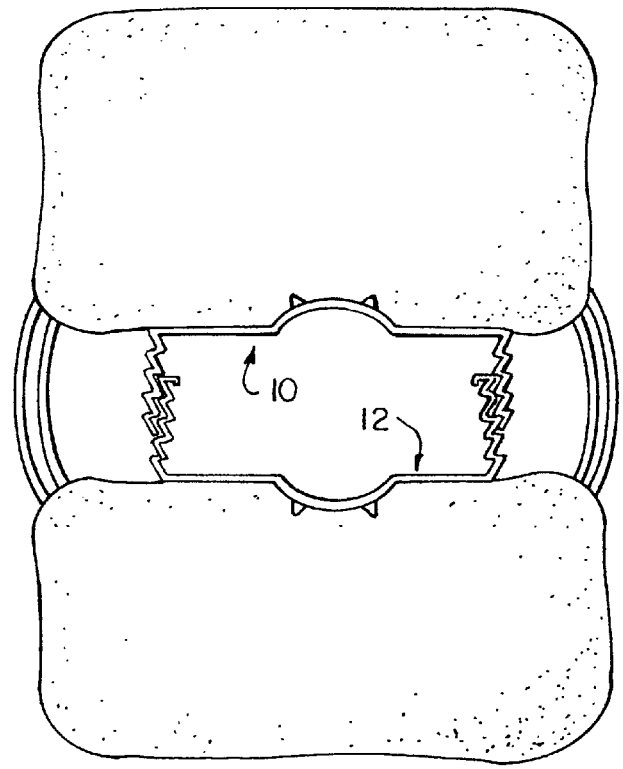
FIG. 5 is a similar view, showing implants which have been expanded between the vertebrae.
Figure 7:
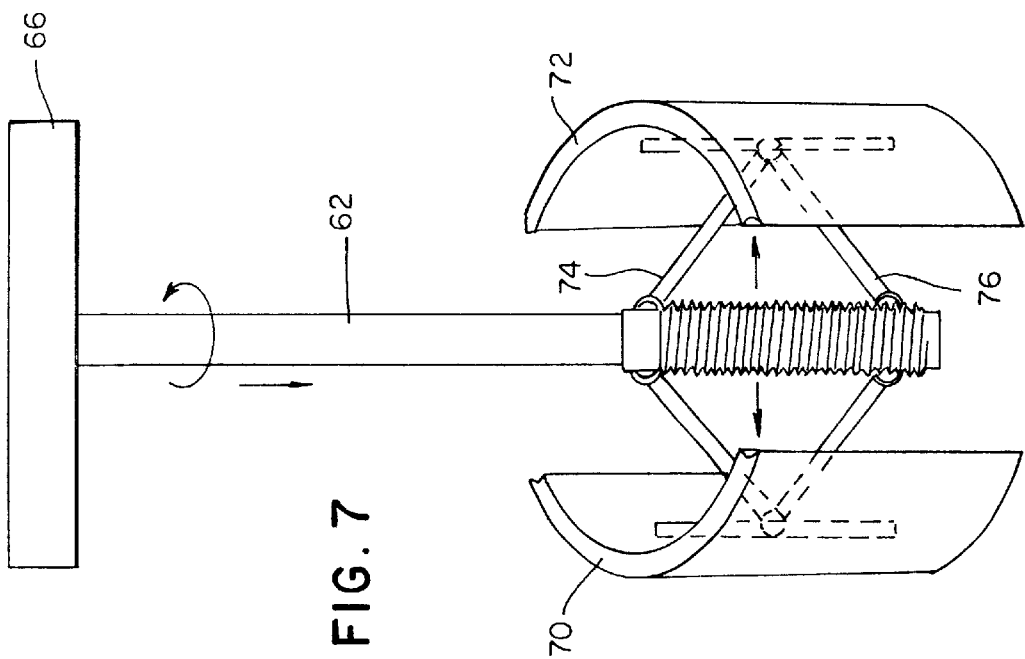
FIGS. 6 and 7 are retracted and expanded views, respectively, of an installation tool.
Figure 6:
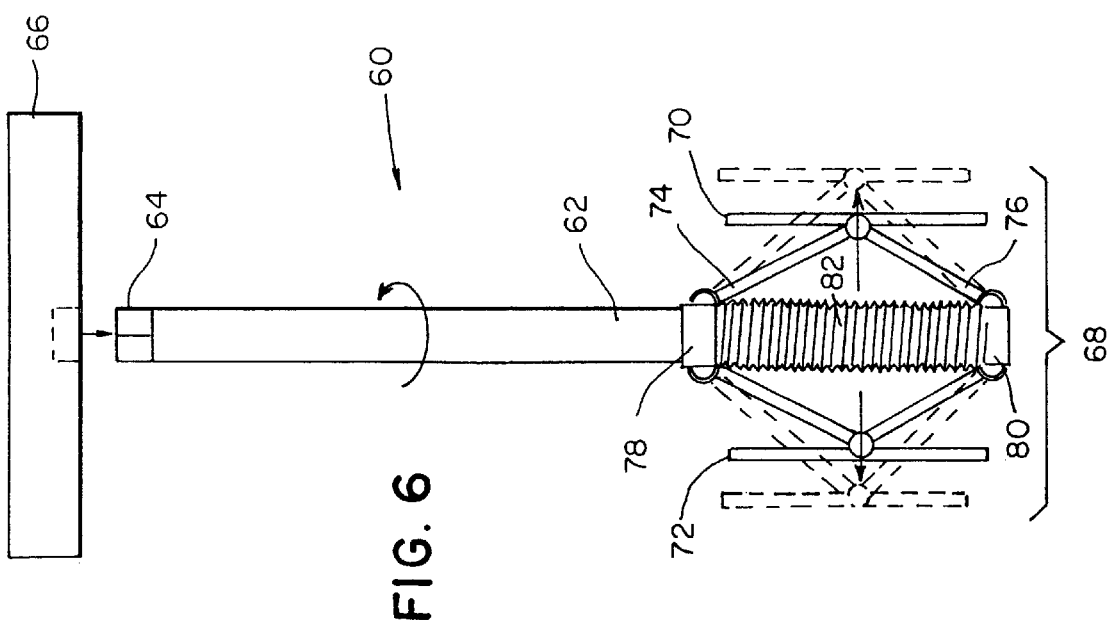

To install an implant, the shells are assembled (FIG. 2) and placed over the jaws of an installation tool (FIGS. 6–7). FIG. 4 shows a pair of implants, unexpanded, situated between a pair of vertebrae. Then the jaws are spread by turning the handle clockwise, forcing the shells outward into contact with the bones above and below. The points on the shells dig into the bony material somewhat to resist accidental dislodgement of the implant subsequently. Once the implant has been adequately expanded, the surgeon manipulates the tool to retract the jaws, and then removes it from within the implant. FIG. 5 shows the implants in their permanent, expanded configuration. It may be observed that the wings on the shells provide a large bearing area against the end plates of the adjacent vertebrae. This is an improvement over prior designs in which the bearing surfaces were only curved.

The installation tool 60 is shown in FIGS. 6 and 7. It includes a shaft 62 having one non-circular end 64 for receiving a removable handle 66. The other end has a radially expandable structure 68, preferably in the form of two jaws 70,72, each of which is connected at its midpoint to the outer ends of a pair of pivoting arms 74,76. The inner ends of these arms are hinged to respective collars 78,80 or the like at the ends of a screw thread 82 on the shaft. The screw mechanism changes the spacing between the collars as the handle is rotated, thus driving the jaws in (FIG. 6) or out (FIG. 7).

The tool may be conveniently used not only to expand the implant in situ, but also to place the implant prior to expansion. The assembled implant (FIG. 2) is placed over the jaws prior to placement. The surgeon can then, using the tools as a manipulator, position the implant in its intended location between vertebrae. Then the handle is turned to expand the implant to its desired final height, and finally the jaws are retracted, so that the tool can be removed from the site.

Since the invention is subject to modifications and variations, it is intended that the foregoing description and the accompanying drawings shall be interpreted as only illustrative of the invention defined by the following claims.

I claim:

1. An expandable intervertebral fusion implant comprising a pair of shells adapted to be assembled to form a hollow body, each of said shells comprising an arcuate central portion, a pair of wings extending in opposite directions from opposite edges of said central portion, and a pair of parallel side walls extending in a common direction from respective outer edges of the wings, and means on the shells for permitting unidirectional expansion of the implant from a retracted initial height to an expanded installed height, wherein each of said wings has a width equal to at least 20% of that of the implant.

2. The invention of claim 1, wherein said means comprises interengaging teeth formed in said side walls.

3. The invention of claim 2, wherein said teeth are corrugations in said side walls, said side walls of one shell being substantially aligned with those of the other shell so that said teeth engage one another.

4. The invention of claim 3, wherein the teeth are raked in one direction so as to permit unidirectional expansion during placement of the implant, but to prevent unintended retraction after placement.

5. The invention of claim 4, wherein the skirts of one of said shells nest within those of the other of said shells, and the inner skirts each have an inwardly protruding element, whereby the inner skirts may be grasped and pulled toward one another in order to disengage the skirts when it is desired to remove the implant.

\* \* \* \* \*